July 9, 1940. W. I. JOHNSTON Plant Pat. 411
ROSE PLANT
Filed March 8, 1940
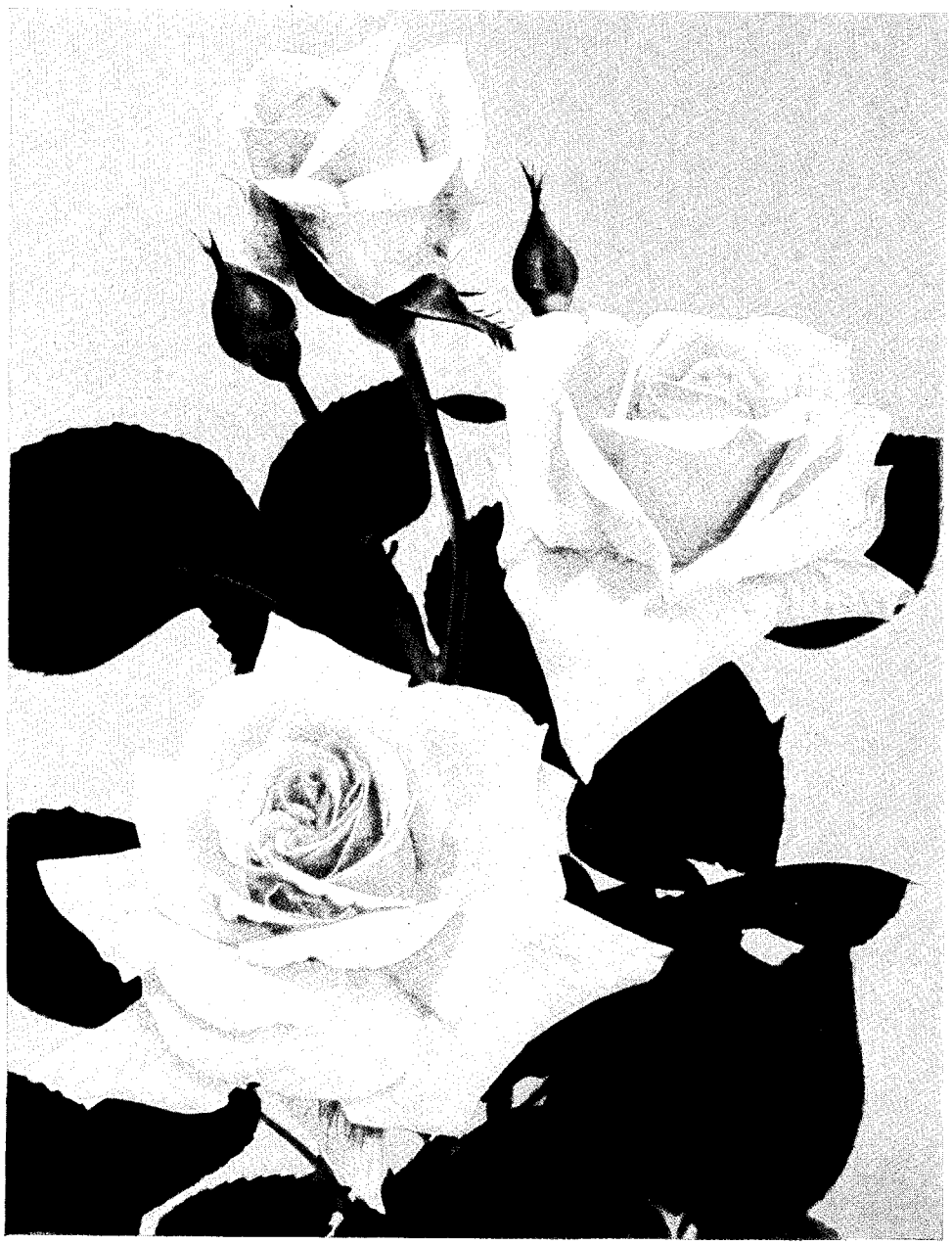
Inventor
Walter I. Johnston
By Robert Robb
Attorneys Patented July 9, 1940

UNITED STATES PATENT OFFICE

411

ROSE PLANT

Walter Irwin Johnston, Portadown, Ireland, assignor to Jackson & Perkins Company, Newark, N. Y.

Application March 8, 1940, Serial No. 323,016

1 Claim. (Cl. 47—61)

The present invention relates to a new and distinct variety of hybrid tea rose plant possessing a number of novel characteristics which go to make a particularly attractive rose among those in the pink range of coloring.

Primarily, this rose is distinctive on account of the Thulite Pink color which appears to be intensified by the Spinel Pink coloring of the reverse side of the petals. It is also distinguished by virtue of the fact that the bud, when the sepals first divide, is Rose Red, and such color combinations, together with the large size and high centered shape of the flower, materially enhance the attractiveness of this variety.

In addition to the foregoing, the plant itself is remarkable because of the vigor of growth and size of foliage for a rose of that color of flower. The young foliage of the plant is distinctively marked with Madder Brown edges and Cress Green center of the leaves.

The new variety has been asexually reproduced and its novel characteristics have been found to come true to form.

The following is a detailed description of the new variety, all color terminology being in accord with Ridgway's Color Standard.

Parentage:

*Seed parent.*—John Henry.

*Pollen parent.*—Portadown Fragrance.

Classification: Botanic and commercial—hybrid tea.

*Flower*

(Observations made in fields and gardens of Jackson & Perkins Company, Newark, New York, in the morning of September 6, 1939.)

Blooming habit: Recurrent—continuous.

Bud:

*Size.*—Medium.

*Form.*—Ovoid. Is not affected by hot weather, or by wet weather.

*Color.*—When sepals first divide—Rose Red, Plate 12. When petals begin to unfurl—between Rose Red, Plate 12, and Spinel Red, Plate 26. When half blown: inside of petals—Thulite Pink, Plate 26; reverse of petals—Spinel Red, Plate 26.

*Sepals.*—Branched. Curl back when flowers half open.

*Calyx.*—*Shape*—funnel. *Size*—broad. *Aspect*—smooth.

*Peduncle.* — *Length* — medium. *Aspect* — prickly. *Color*—Light Cress Green, Plate 31, slightly tinged with Madder Brown, Plate 13. *Strength*—erect, heavy.

*Opening.*—Bud opens well. Is not affected by adverse conditions.

Bloom:

*Size*—large. Average size when fully expanded—4½ inches.

*Borne.*—Singly with side buds.

*Stems.*—Medium length; strong.

*Form.*—When first open—high center. Permanence—retains its form to the end.

*Petalage.*—Very double (many petals and stamens hidden). Number of petals under normal conditions—50.

*Color.*—Center of flower—Spinel Pink, Plate 26. Outer petals—Thulite Pink, Plate 26. Base of petals (aiglet)—Citron Yellow, Plate 16. Inside of petals—between Thulite Pink, Plate 26, and Spinel Pink, Plate 26. Reverse of petals—Spinel Pink, Plate 26. General tonality from a distance—Spinel Pink, Plate 26.

*Discoloration.*—General tonality at end of first day—Spinel Pink, Plate 26. Second day—Spinel Pink, Plate 26, and Thulite Pink, Plate 26. Third day—Thulite Pink, Plate 26.

Petals:

*Texture.*—Thick, soft. Is not affected by wet or hot weather.

*Appearance.*—Inside and outside—satiny.

*Form.*—Oval, scalloped.

*Arrangement.*—Informal (with "rags" in center). *Petaloids in center*—many, small.

*Persistence.*—Drop off cleanly.

*Fragrance.*—Strong. *Nature*—fruity (Russet apple).

*Lasting quality.*—On the plant and as cut flowers—long.

Genital Organs:

*Stamens, anthers.*—*Size*—medium; many. *Color*—Primuline Yellow, Plate 16. *Arrangement*—tucked in calyx.

*Stamens, filaments (threads).*—Medium length.

*Pollen.*—Mustard Yellow, Plate 16.

*Styles*—Loosely separated, uneven length; long; thin; Spinel Red color, Plate 26.

*Stigmas.*—Mustard Yellow, Plate 16.

*Ovaries.*—Some protruding from calyx.

*Plant*

Form: Bush.

Growth: Vigorous.

Foliage: 5 leaflets.

*Size.*—Medium.

*Quantity.*—Normal.

*Color.—New foliage*: upper side—edges Madder Brown, Plate 13, center Cress Green, Plate 31; under side—Van Dyke Red, Plate 13, edges: center Light Cress Green, Plate 31. *Old foliage*: upper side—Dark Cress Green, Plate 31, with veining; under side—Light Cress Green, Plate 31.

*Shape.*—Pointed.

*Texture.*—Upper side—leathery. Under side—smooth. *Ribs and veins.*—Ordinary, with Madder Brown, Plate 13, tinting of leaf stem carrying up into the mid-rib.

*Edge.*—Serrated (saw-toothed).

*Serration.*—Single, small.

*Rachis.*—Color—Madder Brown, Plate 13, the upper side. Under side—smooth; Rainette Green, Plate 31.

*Stipules.*—Medium length; bearded.

*Disease resistance.*—Resistant.

Wood:

*New wood.*—Light Cress Green, Plate 31, slightly tinged with Madder Brown, Plate 13. *Bark*—smooth.

*Old wood.*—Cress Green, Plate 31. *Bark*—smooth.

Thorns (divided into thorns, prickles and short needles):

*Thorns.*—Quantity on main stalks from base and on laterals from stalk—ordinary. *Form*—broad base; hooked downward. *Color when young*—Madder Brown, Plate 13. *Position*—irregular.

*Prickles.*—On main stalks and on laterals—few. *Color*—Madder Brown, Plate 13.

*Short needles.*—Quantity on main stalks—few.

I claim:

A new and distinct variety of rose plant characterized as to novelty by the combination coloring of the bud and flower, its size and high centered shape for a flower of such coloring, and the vigor of growth, size of foliage, and marking of the young foliage, substantially as shown and described.

WALTER IRWIN JOHNSTON.